Figure 1:
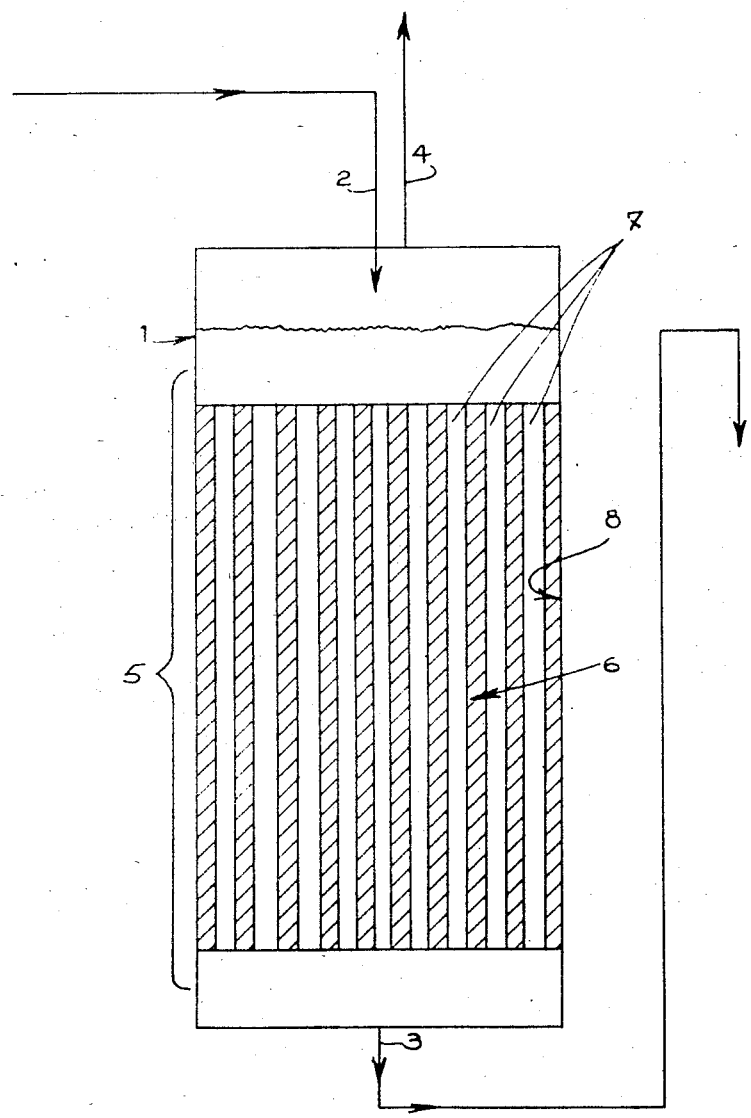

United States Patent [19]

Peters

[11] Patent Number: 4,604,361
[45] Date of Patent: Aug. 5, 1986

[54] REACTOR FOR PRODUCING GAS BY MEANS OF MICRO-ORGANISMS

[75] Inventor: Roeland H. Peters, Standbridge East, Canada

[73] Assignee: Agropur Cooperative Agro-Alimentaire, Granby, Canada

[21] Appl. No.: 480,104

[22] Filed: Mar. 29, 1983

[51] Int. Cl.[4] .......... C12M 1/40; C12M 1/02; B01J 1/00
[52] U.S. Cl. .................. 435/288; 435/287; 435/316; 435/813; 435/819; 422/191; 422/194
[58] Field of Search ............ 435/287, 288, 813, 819, 435/316, 166; 422/115, 171, 180, 191, 194, 234; 261/114 JP; 210/615

[56] References Cited

U.S. PATENT DOCUMENTS

| | | | |
|---|---|---|---|
| 3,068,155 | 12/1962 | Stich | 435/813 X |
| 3,717,552 | 2/1973 | Hondermarck et al. | 435/314 X |
| 3,824,151 | 7/1974 | Iijima et al. | 435/314 X |
| 3,847,750 | 11/1974 | Ridgway, Jr. et al. | 435/813 X |
| 4,016,293 | 4/1977 | Coughlin et al. | 426/42 |
| 4,048,018 | 9/1977 | Coughlin et al. | 435/44 |
| 4,051,011 | 9/1977 | Miyauchi et al. | 204/299 R |
| 4,209,591 | 6/1980 | Hendricks | 435/288 |
| 4,248,972 | 2/1981 | Fischer et al. | 435/292 |
| 4,256,837 | 3/1981 | Fluri et al. | 435/167 |
| 4,286,065 | 8/1981 | Kaluniants et al. | 435/315 |

Primary Examiner—Robert J. Warden
Assistant Examiner—Shawn P. Foley
Attorney, Agent, or Firm—Schwartz, Jeffery, Schwaab, Mack, Blumenthal & Evans

[57] ABSTRACT

A column reactor, suitable for continuous production of a gaseous reaction product by contacting a liquid reaction medium with a gas-forming agent fixed to a reaction plug comprising a solid substrate provided with a plurality of gas-forming channels. The column reactor overcomes the apparent short circuiting of liquid reaction medium through the reactor by being provided with two or more reaction zones, each zone having its own circulatory by-pass means for liquid reaction medium. To obtain the reaction zones a reaction plug can be divided into two or more spaced apart plug portions. For each reaction zone the circulatory by-pass means provides a portion of the pathway for an internal recirculation current of liquid reaction medium.

16 Claims, 5 Drawing Figures

REACTOR FOR PRODUCING GAS BY MEANS OF MICRO-ORGANISMS

The present invention relates to a reactor which can be used for the continuous production of a gaseous reaction product.

Gaseous reaction products may be obtained from a process involving contacting a liquid reaction medium with a gas-forming agent, see for example, LETTINGA, G., VAN VELSEN, A. F. M., HOBMA, S. W., DE ZEEUW, W., KLAPWYK, A., "Use of the Upflow Sludge Blanket Reactor Concept for Biological Wastewater Treatment, Especially for Anaerobic Treatment";
HEERTJES, P. M., VAN DER MEER, R. R., "Comparison of different methods for anaerobic treatment of dilute wastewaters", Proceedings Purdue University Industrial Waste Conference 1979, Ann Arbor Science Publishers; JERIS, J. S., et AL., "Biological fluidized bed treatment for BOD and nitrogen removal", JWPCF 49, 816 (1977); JEWELL, W. J., SWITZENBAUM, M. S., MORRIS, J. W. "Sewage treatment with the anaerobic attached microbial film expanded bed process", 52nd Annual Water Pollution Control Federation Conference, Houston, Texas, 1979; CRAWFORD, G. V., ALKERNA, T., YUE, M., THORNE, M. "Treatment of high strength liquors from sludge thermal conditioning systems using anaerobic packed bed reactors", 53rd Annual Conference of the Water Pollution Control Federation, Las Vegas, Nevada, 1980; and STEVENS, T. G., VAN DEN BERG, L. "Anaerobic Treatment of Food Processing Wastes using a Fixed Film Reactor", Proceedings Purdue University Industrial Waste Conference 1981, Ann Arbor Science Publishers. The gas-forming agent may be selected from the group consisting of suitable microorganisms, enzymes and catalysts. The liquid reaction medium may be a suitable fermentation medium. The gaseous reaction product may be methane.

As energy costs increase, it becomes important to be able to take advantage of every concievable source of energy. Thus in recent times a great deal of attention has been given to the use of methane which can be obtained from materials which are by-products of other processes.

Thus with respect to the dairy industry, it is possible to obtain methane from a fermentation medium consisting of a solution of lactose in water, suspended proteins, milk fat, lactic acid and other dairy waste, the medium being contacted with various strains of methanobacter; for more details see for example SWITZENBAUM, M. S., DANSKIN, S. C., NADAS, D. "Methane generation from whey for energy production and pollution control", Proceedings, Energy Optimization of Water and Wastewater Conference, U.S. Dept. of Energy, New Orleans 1979.

A number of reactors are available which can be used for the production of gaseous reaction product. Known reactors include, mixed tank reactors, fluidized bed reactors, packed bed reactors, and fixed film reactors; see for example U.S. Pat. No. 4,256,837, Fluri et al, Mar. 17, 1981 and U.S. Pat. No. 4,248,972, Fischer et al, Feb. 3, 1981.

Reactors suitable for the production of gaseous product can be split into two groups: a first type wherein the gas-forming agent is dispersed in the liquid reaction medium; and a second type wherein the gas-forming agent is fixed or immobilized to a suitable solid substrate or carrier. The immobilization of active elements to solid insoluble carriers is known; for example, enzymes have been fixed to substrates in order to effect other types of processes, see the following United States Patents:

| 4 051 011 | Miyauchi et al | September 27, 1977 |
| 4 209 591 | Hendriks | June 24, 1980 |
| 4 048 018 | Coughlin et al | September 13, 1977 |
| 4 016 293 | Coughlin et al | April 5, 1977 |

The first type of reactor may be satisfactory for some types of batch operations. However, if the reactor is to be used in a continuous operation which involves the reuse of the gas-forming agent, the gas-forming agent must be of a kind which is recoverable from the treated liquid reaction medium. The recovery of the gas-forming agent can be facilated by filtration or decantation which will of course involve the use of additional equipment. The use of a conventional settler is illustrated in Dutch patent application No. 7,606,904 published on Dec. 28, 1977. The disadvantage of this type of reactor is that it may be difficult or impossible with certain media, for example media containing large amount of dispersed solids, to recover the dispersed gas forming agent.

A mixed tank reactor wherein the gas-forming agent is dispersed in the liquid reaction medium is an example of the first type of reactor.

In accordance with the second type of reactor the gas-forming agent is fixed to a suitable solid substrate by some suitable means, e.g. adsorption. The reactor can be of the fixed bed or fluidized bed type; examples of fluidized bed reactors are illustrated in the previously mentioned U.S. Pat. Nos. 4,209,591 and 4,048,018. These types of reactors can conviently be used for continuous production of gaseous-reaction product since the gas-forming agent is in a form which facilitates its separation from the liquid reaction medium.

A packed bed reactor can also be used to produce gaseous reaction product; the packing material forming the fixed bed or reaction plug has the gas-forming agent fixed thereto. The packing material can be randomly distributed and can be in the form of pebbles, raschig rings, pall rings etc. These types of reactors are, however, susceptible to blockage if the liquid reaction medium contains any solid material; this can lead to the formation of dead spots where there is less or no continuous contact with fresh liquid reaction medium and can eventually possible lead to blockage of the entire bed.

A particular form of a packed bed reactor which substantially overcomes the problem of blockage is known generally as a fixed film reactor. In accordance with one adaptation of this type of reactor the packed bed or plug is provided with a plurality of gas-forming channels (e.g. straight); the plug consists of a suitable solid substrate to which is fixed the gas-forming agent. The liquid reaction medium can be passed through a column reactor incorporating this arrangement in either an upward or downward direction, i.e. in an upward or downward feed mode. In either feed mode the liquid reaction medium is caused to flow through the channels where it contacts the gas-forming agent giving rise to gaseous reaction product. Such an arrangement has been used wherein vitrified clay tile and terra cotta tile has been used as the solid support or solid substrate; L.

Van den Berg: Industrial Waste Conference, Purdue University, Lafayette, Ind., May 12, 13, 14, 1981.

The above adaptation of the fixed film reactor has always been arranged so that the reaction plug or bed is tightly packed against the reactor outer shell wall (i.e. it abuts the outer wall). This has been done in order to avoid having liquid reaction medium by-pass the channels and pass directly to the outlet of the reactor. Such reactors nevertheless present a problem of apparent short circuiting of liquid reaction medium through the channels such that the overall residence time of the liquid reaction medium in contact with the gas-forming agent is less than optimal for a given feed rate.

It would be advantageous to be able to have a column reactor which avoids the apparent short-circuiting of liquid reaction medium through a reactor incorporating a reaction plug of the type as described above.

It has been discovered that the apparent short circuiting of fixed film reactors of the type described above can be overcome by providing a reactor with two or more reaction zones, each zone having its own circulatory by-pass means for liquid reaction medium. To obtain the reaction zones a reaction plug can be divided into two or more spaced apart plug portions. For each reaction zone the circulatory by-pass means provides a portion of the pathway for an internal (i.e. zone) recirculation current of liquid reaction medium. Two or more zones are provided to avoid short-circuiting from inlet to outlet.

In particular the present invention provides a column reactor, suitable for the continuous production of a gaseous reaction product by contacting a liquid reaction medium with a gas-forming agent fixed to a solid substrate, having an outer shell wall, inlet means for feeding liquid reaction medium into the reactor, outlet means for recovering gaseous reaction product, outlet means for recovering treated liquid reaction medium and at least two reaction zones following one after the other, said reactor being characterized in that each reaction zone comprises a first free volume a reaction plug and a second free volume disposed within said outer shell wall, wherein said first free volume is spaced apart from said second free volume by said reaction plug, wherein said reaction plug, consisting of a suitable solid substrate, is provided with a plurality of gas-forming channels, the walls of said channels having a gas-forming agent fixed thereto, said plug having a periphery adjacent to the outer shell wall, wherein said reaction zone is adapted so that fluid communication between said first free volume and said second free volume is provided by said channels and a circulatory by-pass means adapted to allow liquid reaction medium to by-pass said channels, wherein said channels and said by-pass means are adapted to co-operate to facilitate the circulation of an internal current of liquid reaction medium, between said free volumes through said circulatory by-pass means and channels as defined above, and wherein the second free volume of a reaction zone is in fluid communication with the first free volume of the following reaction zone.

If desired, or if necessary, the by-pass means may be adapted to additionally include some suitable pumping means to provide, or to participate in the inducement of, the internal recirculation current.

In accordance with the present invention, it is possible to use the column reactor in either the downflow or the upflow mode. In both modes, the inherent pumping action of gaseous reaction product rising through the gas-forming channels induces the internal recirculation current for each reaction zone. Gas bubbles rising upwardly in the gas-forming channels will induce a liquid current which tends to displace liquid reaction medium upwardly. The by-pass means for a reactor used in the downward feed mode, for example, is thus adapted to facilitate the downward flow of liquid reaction medium.

Thus the present invention provides a column reactor, suitable for the continuous production of gaseous reaction product by contacting a downwardly flowing liquid reaction medium with a gas-forming agent fixed to a solid substrate, having an outer shell wall, inlet means for feeding liquid reaction medium into the reactor, outlet means for recovering gaseous reaction product, outlet means for recovering treated liquid reaction medium and at least two reaction zones following one after the other, said reactor being characterized in that each reaction zone comprises, a first upstream free volume, a reaction plug, and a second downstream free volume, disposed within said outer shell wall, wherein said first free volume is spaced apart from said second free volume by said reaction plug, wherein said reaction plug, consisting of a suitable solid substrate, is provided with a plurality of gas-forming channels, the walls of said channels having a gas-forming agent fixed thereto, said plug having a periphery adjacent to the outer shell wall, wherein said reaction zone is adapted so that fluid communication between said first free volume and said second free volume is provided by said channels and a circulatory by-pass means adapted to allow liquid reaction medium to by-pass said channels, wherein said channels and said by-pass means are adapted to co-operate to facilitate the circulation of an internal current of liquid reaction medium, said internal current being induced by gaseous reaction product rising through gas-forming channels into said first free volume, said internal current flowing through gas-forming channels into said first volume then through said by-pass means into said second free volume back to gas-forming channels, and wherein the second free volume of a reaction zone is in fluid communication with the first free volume of the following reaction zone.

In accordance with the present invention the gas-forming channels may take any suitable configuration. For example the plug may comprise a plurality of spaced apart plates (e.g. flat or corrugated) and the gas-forming channels may be defined by the opposing surfaces of said plates. Alternatively the gas-forming channels may have a cylindrical configuration.

In accordance with an embodiment of the present invention at least a portion of said periphery may be spaced apart from said outer shell wall, said circulatory by-pass means comprising at least one channel defined by said portion of said periphery and said outer shell wall.

In accordance with another embodiment of the invention said periphery may be spaced apart from said outer shell wall, said circulatory by-pass means comprising an annular channel defined by said periphery and said outer shell wall.

In accordance with a further embodiment of the present invention said periphery may abut said outer shell wall, said circulatory by-pass means comprising at least one pipe disposed outside said shell wall, said pipe being in fluid communication with said first and second free volumes.

In accordance with an additional embodiment of the present invention the periphery of the plug may abut said shell wall and said by-pass means may comprise at least one by-pass channel provided in said plug in addition to said gas-forming channels, said by-pass channel may have a cylindrical configuration.

The column reactor in accordance with the present invention can in particular be used to obtain methane from lactose. The solid substrate can be clay tile, terra cotta, wood slats, concrete blocks, corrugated asbestos-cement sheets, corrugated fiberglass reinforced polyester sheets. The gas-forming agent can be selected from micro-organisms, enzymes and catalysts such as Methanobacter, Methanobrevibacter, etc., saccharomyces cerevisiae, *Kluyveromyces fragilis, Candida pseudotropicales.*

Typically biological gas production occurs at temperatures either in the psychophilic range, to 20° C., the mesophilic range 20° C. to 45° C. or in the thermoplilic range 45° C. to 65° C. at a constant pH in the range of 4 to 11 and most often around 7.

The column reactor must contain at least two reaction zones. Preferably it contains 2 to 5 reaction zones.

Typically a gas-forming channel (e.g. of cylindrical configuration) has a cross-sectional area smaller than a channel used for the by-pass means. The gas-forming channels can have a width or diameter in the range at 10 to 50 mm. The by-pass means has a nominal diameter or width which is larger than that of a channel so as to allow a larger flow of current therethrough than through a gas-forming channel. The respective widths of the gas-forming channels and the by-pass means are selected so that the by-pass means can accommodate the internal recirculation stream for a particular reaction zone. Typically the channel width is 20 to 60 mm while the by-pass channel has a diameter or width of 100 to 400 mm.

Figure 2:
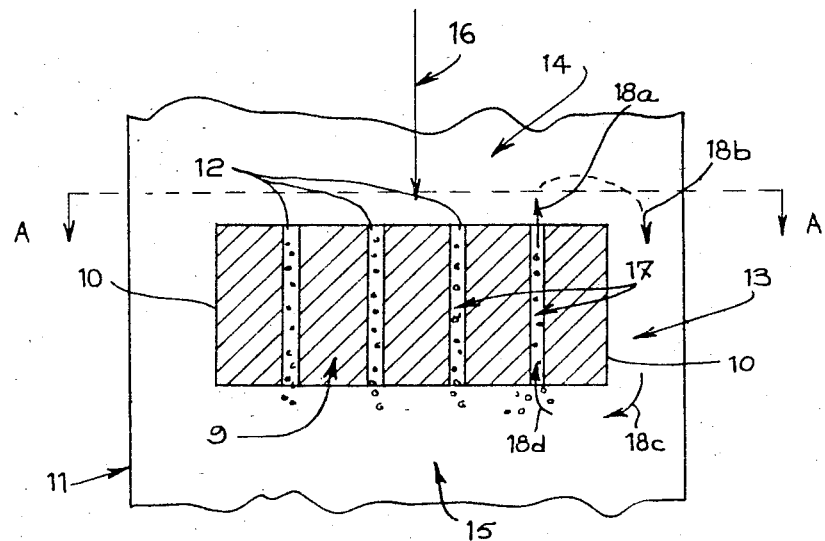
Figure 3:
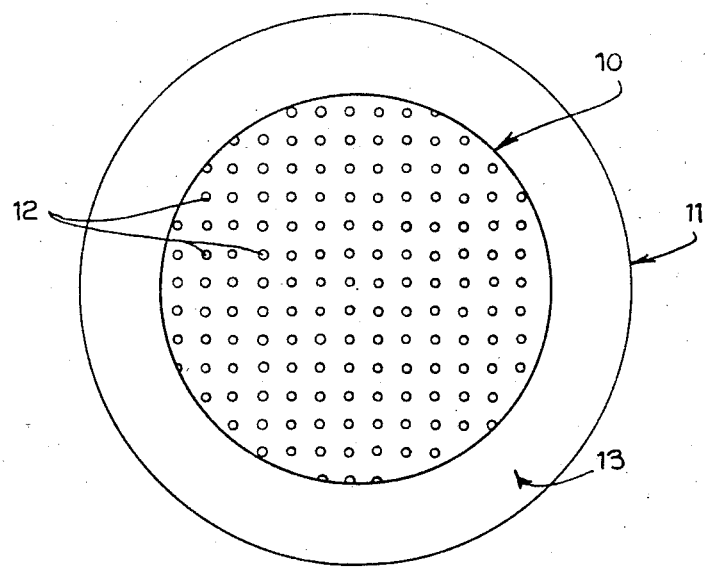
Figure 4:
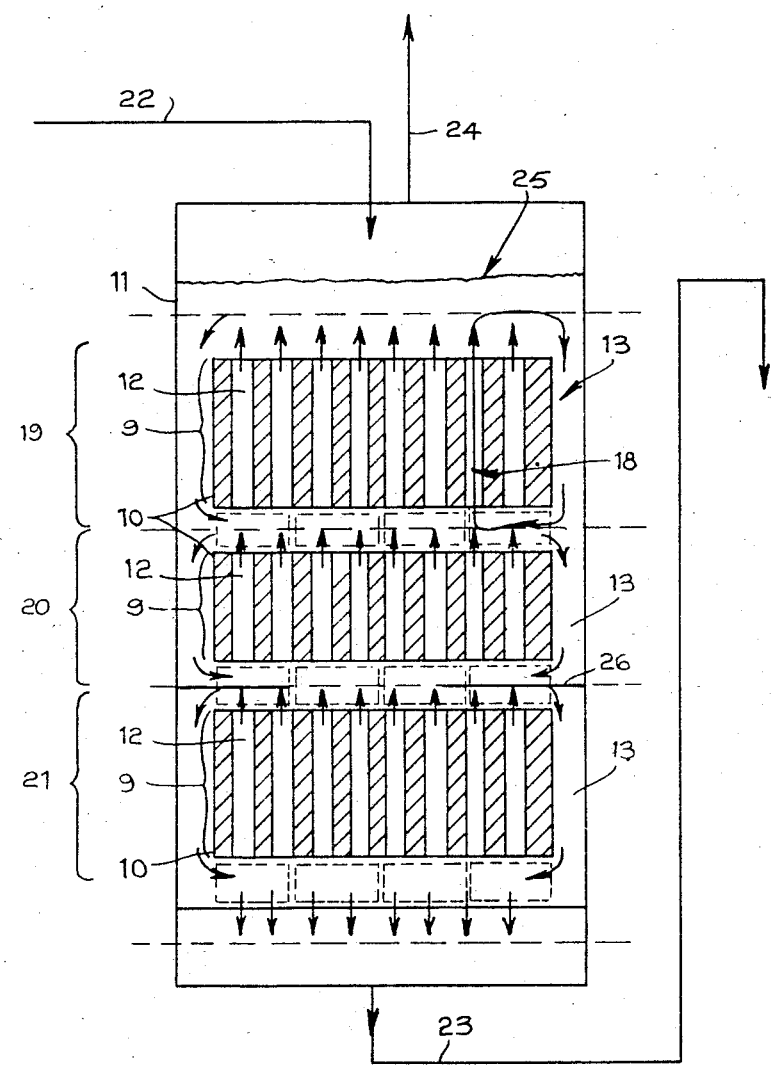
Figure 5:
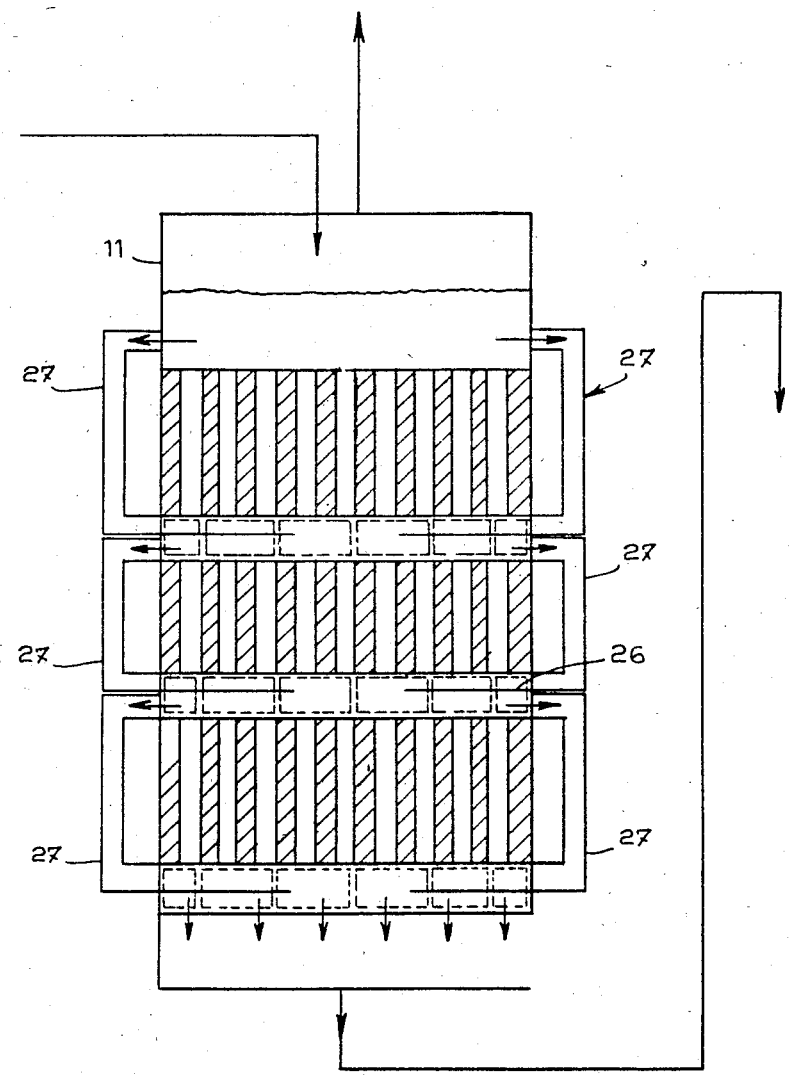

Embodiments of the present invention will be now discussed with respect to the following figures in which, FIG. 1 is a side view of a known fixed-film reactor, FIG. 2 is a side view of a reaction zone in accordance with the present invention, FIG. 3 is a top view along A A of the side view illustrated FIG. 2, FIG. 4 illustrates a column reactor in accordance with the present invention which incorporates reaction zones as illustrated in FIG. 2, FIG. 5 illustrates another column reactor in accordance with the present invention using different by-pass means than illustrated in FIG. 4.

The reactor illustrated in FIG. 1 has an outer shell wall 1 and is adapted to provide outlet and inlet streams for liquid reaction medium and reaction products indicated generally by the numbers 2, 3 and 4 respectively. The reactor is in a substantially vertical position and is used in a downward feed mode, i.e. the liquid reaction medium is introduced at the top of the reactor thru stream 2, treated liquid reaction medium is recovered as stream 3 and gaseous reaction product is recovered as stream 4.

The known reactor comprises a single reaction zone indicated generally at 5. The reaction zone 5 includes a single reaction plug 6 which consists of a solid substrate provided with a plurality of substantially straight gas-forming channels indicated generally as 7. The solid substrate has fixed thereto the desired gas-forming agent i.e. micro-organism, enzyme, catalyst, etc. The periphery 8 of the reaction plug 6 abuts the outer shell wall 1; i.e. reaction medium entering inlet 2 must pass through the gas-forming channels 6 in order to be recovered at the outlet 3.

FIGS. 2 and 3 represent a cross-sectional view of a single reaction zone of a column reactor in accordance with the present invention. The reaction zone has a reaction plug 9, the periphery 10 of which is spaced apart from the outer shell wall 11 of the reactor. The reaction plug 9 includes a plurality of straight gas-forming channels indicated generally by 12. The by-pass means for this embodiment comprises an annular or ring-like channel 13 defined by the periphery 10 and the outer shell wall 11; as indicated above the by-pass means can be included within the reaction plug or be provided on the exterior of the outer shell wall 11. The first free volume indicated generally at 14 is spaced apart from the second free volume indicated generally at 15 by the reaction plug 9. The free volumes 14 and 15 represent volumes within the outer shell wall 11 which are not occupied by the reaction plug 9; i.e. during use these volumes are filed with liquid reaction medium. The reactor plug 9 consists of a suitable solid substrate to which is fixed the desired gas-forming agent.

The operation of the reaction zone illustrated in FIGS. 2 and 3 using a downward feed mode is as follows: The liquid reaction medium passes through the reaction zone in a substantially vertical direction indicated generally by the arrow 16. Gaseous reaction product formed in the gas-forming channels 12 forms gas bubbles 17 which rise through the channels 12 to the free volume 14. The internal recirculation current is indicated at 18a, 18b, 18c and 18d with respect to one gas-forming channel and the annular channel 13. As the gas bubbles 17 rise through the gas-forming channel they induce an upward current of liquid reaction medium indicated at 18a. The current passes into the free volume 14 and then into the annular channel 13 generally as indicated at 18b. The recirculation current flows thereafter into the free volume 15 as indicated generally at 18c and then it goes back to the gas-forming channel at 18d to complete the circuit. Thus the reaction zone effectively allows for a circular movement of liquid reaction medium therethough.

It is to be understood that the parameters such as the liquid reaction medium feed rate and the respective sizes of the channels and by-pass means are selected such that the upward flow of the liquid reaction medium indicated at 18a is stronger than the overall flow of the liquid reaction medium through the reaction zone, the downward flow being generally facilitated by the by-pass means.

FIG. 4 illustrates a column reactor in accordance with the present invention which has 3 reaction zones as illustrated in FIGS. 2 and 3. These reaction zones are indicated generally at 19, 20 and 21. Each of the zones includes a reaction plug 9 and a plurality of straight gas-forming channels indicated generally by 12. The by-pass means consists of the annular ring indicated generally at 13.

The column reactor illustrated in FIG. 4 can be operated in a downward feed mode in which case the reactor is disposed so that the straight channels are more or less vertically inclined. For the downward feed mode the liquid reaction medium is introduced into the reactor by inlet stream 22, the treated liquid reaction medium is recovered as outlet stream 23 and the gaseous product is recovered as outlet stream 24. The top level of the liquid reaction medium in the reactor is indicated by 25. As can be seen the second (downstream) free volume and the first (upstream) free volume for reaction zones 19 and 20 (or 20 and 21) are generally indistinguishable one from the other. The arrows in the reactor pointing upstream generally designate the flow of gaseous reaction product whereas the downstream pointing arrows indicate the general flow of liquid reaction medium. A recirculation current is indicated generally at 18.

In operation the liquid reaction medium is fed downwardly through the reaction zones. As the reactions proceed gas bubbles formed in the gas-forming channels rise upwardly through these channels and induce internal recirculation currents in each of the zones i.e. as indicated generally at 18.

If desired, or if necessary, the reactor may include a suitable baffle which is adapted so that it does not interfere with the rising gas bubbles but facilitates the horizontal or radial flow of liquid reaction medium in the free volumes. The baffle, may for example, be placed in the reactor as indicated in the FIG. 4 by the reference numeral 26; the baffle 26 extends from the outer shell wall to a desired point in the free volume between respective reaction plugs.

FIG. 5 illustrates another embodiment of the present invention. In accordance with this embodiment the peripheral walls of each reaction plug abuts the outer shell wall. The by-pass means comprises piping generally indicated by 27; the piping 27 is disposed on the exterior part of the outer shell wall 11. Apart from the above the reactor is arranged as for the embodiment illustrated in FIG. 4.

The gas-forming channels illustrated in the figures are shown as having a cylindrical configuration with a circular cross section. These channels may, however, have any cross sectional shape e.g. square, rectangular, triangular, etc.. These channels as indicated above may also be defined by suitably spaced apart plates (e.g. parallel).

The surface of the by-pass means may if desired also have a gas-forming agent fixed thereto provided that the surface to volume ratio of the by-pass means is substantially lower than that for the gas-forming channels i.e. the gas formed therein does not impede the function of the by-pass means.

The gas-forming channels in the above described embodiments provides a more or less straight route for the evolved gas and the liquid medium. The channels can provide a less direct route (i.e. a tortuous route) provided that there is no interference with the evolution of the gas and the internal circulating currents.

A column reactor in accordance with the present invention may be used to treat a liquid reaction medium consisting of an aqueous solution of hydrocarbons including lactose (in a concentration of 0.4% by weight). If methanobacter is used as the gas-forming agent and if the gas-forming channels have a nominal width of 42 mm. and the by-pass channels having a nominal width of 300 mm., the liquid reaction medium may be fed into the reactor at a rate of about 0.1 mm per second.

The embodiments of the invention in which an exclusive property or privilege is claimed are defined as follows:

1. A column reactor for continuous production of a gaseous reaction product by contacting a downwardly flowing liquid reaction medium with a gas-forming agent fixed to a solid substrate, said reactor comprising an outer shell wall, inlet means for feeding liquid reaction medium into the reactor, outlet means for recovering gaseous reaction product, outlet means for recovering treated liquid reaction medium, and at least two reaction zones disposed within said outer shell wall following one after the other; wherein each reaction zone includes a first upstream free volume, a reaction plug consisting of a solid substrate provided with a plurality of gas-forming channels and having a periphery adjacent the outer shell wall, and a second downstream free volume spaced apart from said first free volume by said reaction plug; said gas-forming channels communicating between the first free volume and the second free volume and having a gas-forming agent fixed to the walls thereof; each reaction zone further being provided with a circulatory by-pass means communicating between said first and second free volumes for allowing liquid reaction medium to by-pass said channels; said channels and said by-pass means together facilitating an internal circulation of liquid reaction medium rising through the gas-forming channels into said first free volume under the influence of gaseous reaction product and passing from said first free volume through said by-pass means and the second free volume back to said gas-forming channels, and wherein the first free volume of each following reaction zone is in fluid communication with the second free volume of the preceding reaction zone.

2. A column reactor as defined in claim 1, wherein said plug comprises a plurality of spaced apart plates and said gas-forming channels are defined by opposing surfaces of said plates.

3. A column reactor as defined in claim 1, wherein said gas-forming channels have a cylindrical configuration.

4. A column reactor as defined in claim 1, wherein at least a portion of said periphery is spaced apart from said outer shell wall, said circulator by-pass means comprising at least one channel defined by said portion of said periphery and said outer shell wall.

5. A column reactor as defined in claim 1, wherein said periphery is spaced apart from said outer shell wall, said circulatory by-pass means comprising an annular channel defined by said periphery and said outer shell wall.

6. A column reactor as defined in claim 1, wherein said periphery abuts said outer shell wall, said circulatory by-pass means comprising at least one pipe disposed outside said shell wall, said pipe being in fluid communication with said first and second free volumes.

7. A column reactor as defined in claim 1, wherein said liquid reaction medium is a fermentation medium and said gas-forming agent is selected from the group consisting of gas-forming micro-organisms and enzymes.

8. A column reactor as defined in claim 4, wherein said liquid reaction medium is a fermentation medium and said gas-forming agent is selected from the group consisting of gas-forming micro-organisms and enzymes.

9. A column reactor as defined in claim 1, wherein said periphery abuts said outer shell wall, said by-pass means comprising at least one by-pass channel provided in said plug in addition to said gas-forming channels.

10. A column reactor as defined in claim 9, wherein said liquid reaction medium is a fermentation medium and said gas-forming agent is selected from the group consisting of gas-forming micro-organisms and enzymes.

11. A column reactor for continuous production of a gaseous reaction product by contacting a liquid reaction medium with a gas-forming agent fixed to a solid substrate, said reactor comprising an outer shell wall, inlet means for feeding liquid reaction medium into the reactor, outlet means for recovering gaseous reaction product, outlet means for recovering treated liquid reaction medium, and at least two reaction zones disposed within said outer shell wall following one after the other; wherein each reaction zone includes a first free volume, a reaction plug consisting of a solid substrate provided with a plurality of gas-forming channels and having a periphery adjacent the outer shell wall, and a second free volume spaced apart from said first free volume by said reaction plug; said gas-forming channels communicating between the first free volume and the second free volume and having a gas-forming agent fixed to the walls thereof; each reaction zone further being provided with a circulatory by-pass means communicating between said first and second free volumes for allowing liquid reaction medium to by-pass said channels; said gas-forming channels and said by-pass means together facilitating circulation of an internal current of liquid reaction medium between said first and second free volumes through said gas-forming channels and circulatory by-pass means, and the first free volume of each following reaction zone is in fluid communication with the second free volume of the preceding reaction zone.

12. A column reactor as defined in claim 11, wherein said liquid reaction medium is a fermentation medium and said gas-forming agent is selected from the group consisting of gas-forming micro-organisms and enzymes.

13. A column reactor as defined in claim 2, wherein said liquid reaction medium is a fermentation medium and said gas-forming agent is selected from the group consisting of gas-forming micro-organisms and enzymes.

14. A column reactor as defined in claim 3, wherein said liquid reaction medium is a fermentation medium and said gas-forming agent is selected from the group consisting of gas-forming micro-organisms and enzymes.

15. A column reactor as defined in claim 5, wherein said liquid reaction medium is a fermentation medium and said gas-forming agent is selected from the group consisting of gas-forming micro-organisms and enzymes.

16. A column reactor as defined in claim 6, wherein said liquid reaction medium is a fermentation medium and said gas-forming agent is selected from the group consisting of gas-forming micro-organisms and enzymes.

* * * * *